United States Patent
Wang et al.

(10) Patent No.: US 11,978,533 B2
(45) Date of Patent: May 7, 2024

(54) PEPTIDE LIBRARY CONSTRUCTING METHOD

(71) Applicant: HUNAN ZONSEN PEPLIB BIOTECH CO., LTD, Hunan (CN)

(72) Inventors: Zhuying Wang, Hunan (CN); Xiangqun Li, Hunan (CN)

(73) Assignee: HUNAN ZONSEN PEPLIB BIOTECH CO., LTD, Hunan (CN)

( * ) Notice: Subject to any disclaimer, the term of this patent is extended or adjusted under 35 U.S.C. 154(b) by 176 days.

(21) Appl. No.: 16/607,738

(22) PCT Filed: Apr. 26, 2017

(86) PCT No.: PCT/CN2017/082071
§ 371 (c)(1),
(2) Date: Oct. 24, 2019

(87) PCT Pub. No.: WO2018/195834
PCT Pub. Date: Nov. 1, 2018

(65) Prior Publication Data
US 2020/0135299 A1  Apr. 30, 2020

(51) Int. Cl.
*G16B 35/10* (2019.01)
*C12N 15/10* (2006.01)
*C40B 50/06* (2006.01)

(52) U.S. Cl.
CPC ......... *G16B 35/10* (2019.02); *C12N 15/1093* (2013.01); *C40B 50/06* (2013.01)

(58) Field of Classification Search
CPC .......................... G16B 35/10; C12N 15/1093
See application file for complete search history.

(56) References Cited

U.S. PATENT DOCUMENTS

| 7,105,341 B2 * | 9/2006 | Kinsella ...................... 435/320.1 |
| 2009/0175783 A1 * | 7/2009 | Zubeldia et al. .... A61K 51/088 |

FOREIGN PATENT DOCUMENTS

| WO | 0036093 | 6/2000 |
| WO | 0166565 | 9/2001 |
| WO | WO 03/040391 A2 * | 5/2003 |
| WO | 2004020981 | 3/2004 |

OTHER PUBLICATIONS

Downie Ruiz Velasco et al. "Posttranscriptional Regulation of 14q32 MicroRNAs by the CIRBP and HADHB during Vascular Regeneration after Ischemia." Mol Ther Nucleic Acids. 2019; 14:329-338. doi: 10.1016/j.omtn.2018.11.017 (Year: 2019).*
Naumann, T.A. et al; Engineering an Affinity Tag for Genetically Encoded Cyclic Peptides Biotechnol boieng. Sep. 9, 2005, No. 7, vol. 92, p. 820-830.
Townend, J.E. et al; Traceless Production of Cyclic Peptide Libraries in *E. coli* ACS Chem. Biol. Mar. 30, 2016, No. 6, vol. 11, p. 1624-1630.
Scott, C.P., et al; Structural requirements for the biosynthesis of backbone cyclic peptide libraries Chemistry & Biology Jun. 29, 2001, No. 8, vol. 8, p. 810-815.
International Search Report filed in PCT/CN2017/082071 mailed Jan. 22, 2018.

* cited by examiner

*Primary Examiner* — Kaijiang Zhang
(74) *Attorney, Agent, or Firm* — Rankin, Hill & Clark LLP

(57) ABSTRACT

An improved peptide library preparation method is described for constructing complete virtual peptide libraries such as a complete virtual tripeptide library, tetrapeptide library, pentapeptide library, hexapeptide library, heptapeptide library, or a complete octapeptide library, etc. The method includes constructing an expression vector for the expression of cyclic peptides. Each cyclic peptide displays an array of peptides of different sizes and sequences, and the number of cyclic peptides needed for constructing a complete virtual peptide library can be dramatically reduced compared with conventional chemical peptide synthesis. Furthermore, the cyclic peptide libraries can be readily reproduced by the expression and purification of the cyclic peptides using the constructed gene libraries. The improved peptide library preparation method can particularly be used, for example, to construct a complete virtual tetrapeptide library, a complete virtual pentapeptide library, a complete virtual hexapeptide library, a complete virtual heptapeptide library, and so on. The improved peptide library preparation method can also be used, for example, to construct a partial pentapeptide library, a partial hexapeptide library, a partial heptapeptide library, and so on. Other related methods and the related expression vectors are also described.

7 Claims, 3 Drawing Sheets

Specification includes a Sequence Listing.

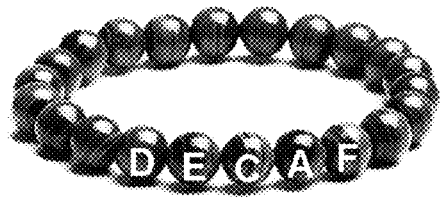

SEQ ID NO: 6

FIG. 1

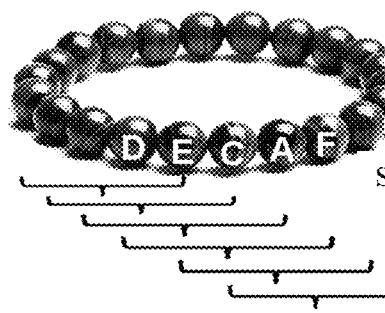

SEQ ID NO: 6

FIG. 2

CWESGKMTGIVKWFNADKGFGFITPDDGSKDVFVHFSAIQNDGYKSLDEGQKVSFTIESGAKGPAAGNVTSLSKTHHHHH (A)  SEQ ID NO: 7

|   | 1 | 2 | 3 | 4 | 5 | 6 | 7 | 8 | 9 | 10 |
|---|---|---|---|---|---|---|---|---|---|---|
| A | CWESG (SEQ ID NO:8) | WESGK (SEQ ID NO:9) | ESGKM (SEQ ID NO:10) | SGKMT (SEQ ID NO:11) | GKMTG (SEQ ID NO:12) | KMTGI (SEQ ID NO:13) | MTGIV (SEQ ID NO:14) | TGIVK (SEQ ID NO:15) | GIVKW (SEQ ID NO:16) | IVKWF (SEQ ID NO:17) |
| B | VKWFN (SEQ ID NO:18) | KWFNA (SEQ ID NO:19) | WFNAD (SEQ ID NO:20) | FNADK (SEQ ID NO:21) | NADKG (SEQ ID NO:22) | ADKGF (SEQ ID NO:23) | DKGFG (SEQ ID NO:24) | KGFGF (SEQ ID NO:25) | GFGFI (SEQ ID NO:26) | FGFIT (SEQ ID NO:27) |
| C | GFITP (SEQ ID NO:28) | FITPD (SEQ ID NO:29) | ITPDD (SEQ ID NO:30) | TPDDG (SEQ ID NO:31) | PDDGS (SEQ ID NO:32) | DDGSK (SEQ ID NO:33) | DGSKD (SEQ ID NO:34) | GSKDV (SEQ ID NO:35) | SKDVF (SEQ ID NO:36) | KDVFV (SEQ ID NO:37) |
| D | DVFVH (SEQ ID NO:38) | VFVHF (SEQ ID NO:39) | FVHFS (SEQ ID NO:40) | VHFSA (SEQ ID NO:41) | HFSAI (SEQ ID NO:42) | FSAIQ (SEQ ID NO:43) | SAIQN (SEQ ID NO:44) | AIQND (SEQ ID NO:45) | IQNDG (SEQ ID NO:46) | QNDGY (SEQ ID NO:47) |
| F | NDGYK (SEQ ID NO:48) | DGYKS (SEQ ID NO:49) | GYKSL (SEQ ID NO:50) | YKSLD (SEQ ID NO:51) | KSLDE (SEQ ID NO:52) | SLDEG (SEQ ID NO:53) | LDEGQ (SEQ ID NO:54) | DEGQK (SEQ ID NO:55) | EGQKV (SEQ ID NO:56) | GQKVS (SEQ ID NO:57) |
| G | QKVSF (SEQ ID NO:58) | KVSFT (SEQ ID NO:59) | VSFTI (SEQ ID NO:60) | SFTIE (SEQ ID NO:61) | FTIES (SEQ ID NO:62) | TIESG (SEQ ID NO:63) | IESGA (SEQ ID NO:64) | ESGAK (SEQ ID NO:65) | SGAKG (SEQ ID NO:66) | GAKGP (SEQ ID NO:67) |
| H | AKGPA (SEQ ID NO:68) | KGPAA (SEQ ID NO:69) | GPAAG (SEQ ID NO:70) | PAAGN (SEQ ID NO:71) | AAGNV (SEQ ID NO:72) | AGNVT (SEQ ID NO:73) | GNVTS (SEQ ID NO:74) | NVTSL (SEQ ID NO:75) | VTSLS (SEQ ID NO:76) | TSLSK (SEQ ID NO:77) |
| I | SLSKT (SEQ ID NO:78) | LSKTH (SEQ ID NO:79) | SKTHH (SEQ ID NO:80) | KTHHH (SEQ ID NO:81) | THHHH (SEQ ID NO:82) | HHHHH (SEQ ID NO:83) | HHHHC (SEQ ID NO:84) | HHHCW (SEQ ID NO:85) | HHCWE (SEQ ID NO:86) | HCWES (SEQ ID NO:87) |

PEPTIDE LIBRARY CONSTRUCTING METHOD

INCORPORATION BY REFERENCE OF SEQUENCE LISTING

The attached sequence listing in computer readable form, which is saved as an ASCII text file by the file name of "SUG-46511—Sequence Listing", created on Aug. 21, 2019, and having a byte size of 1 KB, is incorporated herein by reference.

FIELD OF THE INVENTION

The invention relates to a method for constructing a partial or complete virtual peptide library with cyclic peptides which can display an array of short peptides required for a partial or complete peptide library such as a tetrapeptide library, a pentapeptide library, a hexapeptide library, a heptapeptide library, or an octapeptide library, etc. The method includes constructing an expression vector for the expression of the tagged cyclic peptides. Each tagged cyclic peptide displays an array of peptides of different sizes, and the number of cyclic peptides needed for constructing a partial or complete peptide library can be dramatically reduced relative to conventional chemical peptide synthesis. Furthermore, the libraries can be easily reproduced. The cyclic peptides can also be chemically and enzymatically synthesized to construct a partial or complete virtual peptide library. The improved peptide library preparation method can particularly be used, for example, to construct a complete virtual pentapeptide or hexapeptide library.

BACKGROUND OF THE INVENTION

Peptide libraries, which contain a great number of peptides that have a systematic combination of amino acids, are widely applied as a powerful tool for screening large numbers of peptides in the search for critical bioactive peptides in biological research, protein related study and drug development. Peptides with low molecular weight have been known to be less allergenic and the diverse physiological roles of peptides make them suitable candidates for the development of therapeutic agents (Host A, Halken S. Hypoallergenic formulas—when, to whom and how long: after more than 15 years we know the right indication! Allergy 2004, 59 (Suppl. 78):45-52; Lax R. The future of peptide development in the pharmaceutical industry. Phar Manufacturing: Int Pept Rev 2010; Agyei D, Danquah M K. Industrial scale manufacturing of pharmaceutical grade bioactive peptides. Biotechnol Adv 2011, 29 (3):272-7). Bioactive peptides are therefore suitable candidates for a new era of pharmaceutical products, especially with the heightened concerns of side effects of small molecule drugs and the increased attention to fresher and 'greener' foods and nutraceuticals possessing health-preventing or health-promoting properties (Danquah M K, Agyei D. Pharmaceutical applications of bioactive peptides. OA Biotechnology 2012, 1(2):5).

Many kinds of bioactive peptides have been found, which include antimicrobial, anticancer, antioxidative, antihypertensive, antithrombotic, opioid, antiviral, cytomodulatory and immunomodulatory peptides, etc. (Sharma S, Singh R, Rana S. Bioactive peptide: A Review. Int. J. BioAUTOMATION 2011, 15(4):223-250; Danquah M K, Agyei D. Pharmaceutical applications of bioactive peptides. OA Biotechnology 2012, 1(2):5). Therefore, peptide drug development is one of the most promising fields in the development of the new drugs.

Since a peptide library can provide a powerful tool for drug development, protein-protein interactions, and other biochemical as well as pharmaceutical applications, several methods have been developed to construct peptide libraries. The peptide library construction methods fall into two categories: methods involving synthetic chemistry and methods involving biotechnology approaches.

Introduced in 1985 by George P. Smith, the phage display technology allows the screening of a vast amount of different peptides (Smith, GP. Filamentous fusion phage: novel expression vectors that display cloned antigens on the virion surface. Science 1985, 228:1315-1317). It was found that the success of phage derived peptides essentially depends on the quality of the library screened (Lindner T, Kolmar H, Haberkorn U and Mier W. DNA Libraries for the Construction of Phage Libraries: Statistical and Structural Requirements and Synthetic Methods. Molecules 2011, 16:1625-1641), however, there is no practical method to monitor or guarantee the quality of the phage display library. Indeed, until now only few of the peptides selected by phage display have entered clinical applications (Lindner T, Kolmar H, Haberkorn U and Mier W. DNA Libraries for the Construction of Phage Libraries: Statistical and Structural Requirements and Synthetic Methods. Molecules 2011, 16:1625-1641).

Based on the solid phase synthesis developed by Merrifield, the combinatorial "split-mix synthesis" method was developed for peptide library construction (A. Furka, F. Sebestyen, M. Asgedom, G Dibo, General method for rapid synthesis of multicomponent peptide mixtures. Int. J. Peptide Protein Res., 1991, 37:487-493). Theoretically a huge number of peptides can be synthesized in this way to make a large library, however in practice, the number and quantity of the peptides synthesized in this way is limited due to the high cost and low production yields of synthesizing the library.

Peptides can also be produced by recombinant approaches. Short peptides are usually fused to a protein and then expressed and purified from an expression host such as *E. coli*. (S. Hara, M. Yamakawa, Production in *Escherichia coli* of moricin, a novel type antibacterial peptide from the silkworm, *Bombyx mori*. Biochem. Biophys. Res. Commun. 1996, 224:877-878. H. K. Kim, D. S. Chun, J. S. Kim, C. H. Yun, J. H. Lee, S. K. Hong, D. K. Kang, Expression of the cationic antimicrobial peptide lactoferricin fused with the anionic peptide in *Escherichia coli*. Appl. Microbiol. Biotechnol. 2006, 72:330-338). However in practice, the number and quantity of the peptides produced in this way is also limited due to the long procedure and high cost, and the capacity of peptide library constructed in this way is very low.

Compared to their linear counterparts, cyclic peptides usually show better biological activity due to the conformational rigidity and higher resistance to hydrolysis by exopeptidases due to the lack of both amino and carboxyl termini (Sang Hoon Joo, Cyclic Peptides as Therapeutic Agents and Biochemical Tools. Biomol Ther. 2012, 20 (1):19-26), which make the cyclic peptides better candidates for drug screening. Cyclic peptides can also be produced by either synthetic chemistry or recombinant approaches based on split inteins (Sang Hoon Joo, Cyclic Peptides as Therapeutic Agents and Biochemical Tools. Biomol Ther. 2012, 20 (1):19-26. Manfredi Miraula, Charmaine Enculescu, Gerhard Schenk, Nataša Mitić, Inteins—A Focus on the Biotechnological Applications of Splicing-Promoting Proteins. American Journal of Molecular Biology 2015, 5:42-56). Just like linear peptides produced by recombination approaches, the number and quantity of the cyclic peptides produced in this way is also limited due to the long procedure and high cost, and the capacity of peptide library constructed in this way is low.

A peptide library can be constructed by synthesizing a large number of distinct peptides. Since there is no good way to predict which peptide will be a good drug candidate, it is desired to construct a complete peptide library, which contains all possible combinations of the amino acids, for high chance of finding good drug candidates during peptide screening. There are 20 natural occurring amino acids, 8,000 distinct tripeptides need to be synthesized to construct a complete tripeptide library. In the similar way, 160,000 tetrapeptides need to be synthesized to construct a complete tetrapeptide library, 3,200,000 pentapeptides need to be synthesized to construct a complete pentapeptide library, and 64,000,000 hexapeptides need to be synthesized to construct a complete hexapeptide library. Due to the high cost and low production yields to synthesize the large number of peptides, until now, only a complete tripeptide virtual library (8,000 peptides) containing all possible combinations of the 20 natural amino was synthesized using chemical method for developing a new class of COX-2 inhibitors (Ermelinda V, et al., Design, Synthesis, and Evaluation of New Tripeptides as COX-2 Inhibitors for developing a new class of COX-2 inhibitors. Journal of Amino Acids. 2013, 2013:1-7), a complete tetrapeptide library, which should contain 160,000 tetrapeptides, is even not currently available in the market, not to mention a complete pentapeptide or hexapeptide library and so on.

Thus, there is still a need for a highly productive process for constructing virtual peptide libraries with large capacities. A protein display method was previously described (PEPTIDE LIBRARY CONSTRUCTING METHOD AND RELATED VECTORS, PCT/CN2015/083260) for constructing virtual peptide libraries with large capacities, with which an array of short peptides were displayed at the end of a tag protein such as GST to reduce the number of the peptides needed to build a complete tetrapeptide, pentapeptide or hexapeptide library and so on. However, with the protein display method, each tagged linear peptide, which can display many short peptides, displays much less longer peptides. For example, a tagged linear 50-mer peptide can display 47 tetrapeptides, 46 pentapeptides or 45 hexapeptides, but only two 49-mer peptides and only one 50-mer peptide, limiting the capacity of the library. Therefore, it would be desirable to have a method for constructing virtual peptide libraries with even large capacities.

BRIEF SUMMARY OF THE INVENTION

It is an object of this invention to provide improved methods for constructing virtual peptide libraries with high capacities. Instead of displaying peptides at the end of a protein tag, a linear peptide is cyclized to form a cyclic peptide to display more peptides, thus to increase the capacity of the library. For example, with reasonable designing, a cyclic peptide of 50 amino acids can actually display 50 distinct consecutive tripeptides, 50 distinct consecutive tetrapeptides, 50 distinct consecutive pentapeptides, 50 distinct consecutive hexapeptides, 50 distinct consecutive heptapeptides, and so on, even 50 distinct consecutive 48-mer peptides, 50 distinct consecutive 49-mer peptides and 50 50-mer peptides, which constitutes 2400 different peptides with sizes ranging from 3 to 50 amino acids.

It is another object of this invention to provide an improved method for constructing a complete virtual tetrapeptide library. With reasonable designing, a cyclic peptide of 50 amino acids can actually display 50 distinct consecutive tetrapeptides, only 3,200 cyclic 50-mer peptides instead of 160,000 synthetic tetrapeptides are needed to construct a complete virtual tetrapeptide library by this protein display method. In a similar way, only 2,000 cyclic 80-mer peptides are needed to construct a complete virtual tetrapeptide library. The number of larger cyclic peptides can be further reduced to construct a complete virtual tetrapeptide library.

It is yet another object of this invention to provide an improved method for constructing a complete virtual pentapeptide library. With reasonable designing, a cyclic peptide of 50 amino acids can actually display 50 distinct consecutive pentapeptides, only 64,000 cyclic 50-mer peptides instead of 3,200,000 synthetic pentapeptides are needed to construct a complete virtual pentapeptide library by this protein display method. In a similar way, only 40,000 cyclic 80-mer peptides are needed to construct a complete virtual pentapeptide library. The number of larger cyclic peptides can be further reduced to construct a complete virtual pentapeptide library.

It is yet another object of this invention to provide an improved method for constructing a complete virtual hexapeptide library. With reasonable designing, a cyclic peptide of 50 amino acids can actually display 50 distinct consecutive hexapeptides, only 1,280,000 cyclic 50-mer peptides instead of 64,000,000 synthetic hexapeptides are needed to construct a complete virtual hexapeptide library by this protein display method. In a similar way, only 800,000 cyclic 80-mer peptides are needed to construct a complete virtual hexapeptide library. The number of larger cyclic peptides can be further reduced to construct a complete virtual hexapeptide library.

It is yet another object of this invention to provide an improved method of constructing a virtual peptide library with large capacity using a chemical synthesis approach, the method comprising: (i) designing a series of cyclic peptides with each cyclic peptide displaying an array of short peptides; (ii) synthesizing the linear peptides with the corresponding cyclic peptide sequences with chemical methods with or without purification; (iii) cyclizing the linear peptides to make the cyclic peptides with chemical methods or enzymatic methods; (iv) purifying the cyclic peptides and using the library for screening.

It is yet another object of this invention to provide an improved method of constructing a virtual cyclic peptide library with large capacity, the method comprising: (i) designing a series of cyclic peptides with each cyclic peptide containing an array of short peptides and one or more affinity tags; (ii) constructing a series of expression vectors with each vector expressing a single cyclic peptide; (iii) expressing and purifying the cyclic peptides by binding the affinity tag to a specific ligand immobilized to a solid phase; (iv) eluting the cyclic peptides from the solid phases and using the library for screening; and (v) optionally using the immobilized cyclic peptides directly for screening without being eluted from the solid phases It is yet another object of this invention to provide a method for constructing an incomplete or partial virtual peptide library with a significantly reduced number of cyclic peptides. For longer peptides such as heptapeptides, octapeptides, decapeptides, or even longer peptides such as 15-mer or 20-mer peptides, the complete libraries will contain huge numbers of all possible peptides, which are $1.28 \times 10^9$, $2.56 \times 10^{10}$, $1.024 \times 10^{13}$, $3.277 \times 10^{19}$, $1.049 \times 10^{26}$, respectively. Therefore, it is not practical to chemically synthesize so many peptides to make a complete peptide library. However, it is still desirable to construct a partial virtual library since some peptides will share high sequence similarity. By rational designing, the number of peptides to construct an efficient partial peptide library can be greatly reduced. This method of the invention will further reduce the peptide number in a partial peptide library, thus to make the construction of an efficient peptide library practical.

It is a further object of this invention to provide an alternative method for constructing a complete peptide library. The DNA sequence of each cyclic peptide will be cloned into an expression vector for the expression and purification of the tagged cyclic peptide. The vector can be stored and the peptide can be expressed or reproduced from the vector readily at any time. Unlike peptide synthesis, each peptide needs to be resynthesized from scratch.

It is an object of this invention to provide a method for constructing expression vectors for the expression and purification of the tagged cyclic peptides for the peptide library construction.

Additional objects of the invention are reflected in the original claims. The details of embodiments of the disclosure are set forth in the accompanying drawings and the description below. Other features, objects, and advantages will be apparent from the description and drawings, and from the claims.

BRIEF DESCRIPTION OF THE SEVERAL VIEWS OF THE DRAWINGS

The foregoing brief summary, as well as the following detailed description of the invention, will be better understood when read in conjunction with the appended drawings. For the purpose of illustrating the invention, there are shown in the drawings embodiments which are presently preferred. It should be understood, however, that the invention is not limited by the drawings presented.

In the drawings:

FIG. 1 schematically illustrates that a cyclic peptide can display many shorter peptides, and one pentapeptide, DECAF (Asp-Glu-Cys-Ala-Phe), is shown as an example;

FIG. 2 schematically illustrates the high capacity of cyclic peptides for displaying short peptides according to an embodiment of the invention;

FIG. 3(A) and FIG. 3(B) schematically illustrate a typical example of 80 different pentapeptides displayed by a single cyclic 80-mer cyclic peptide;

DETAILED DESCRIPTION OF THE INVENTION

Figure 4:
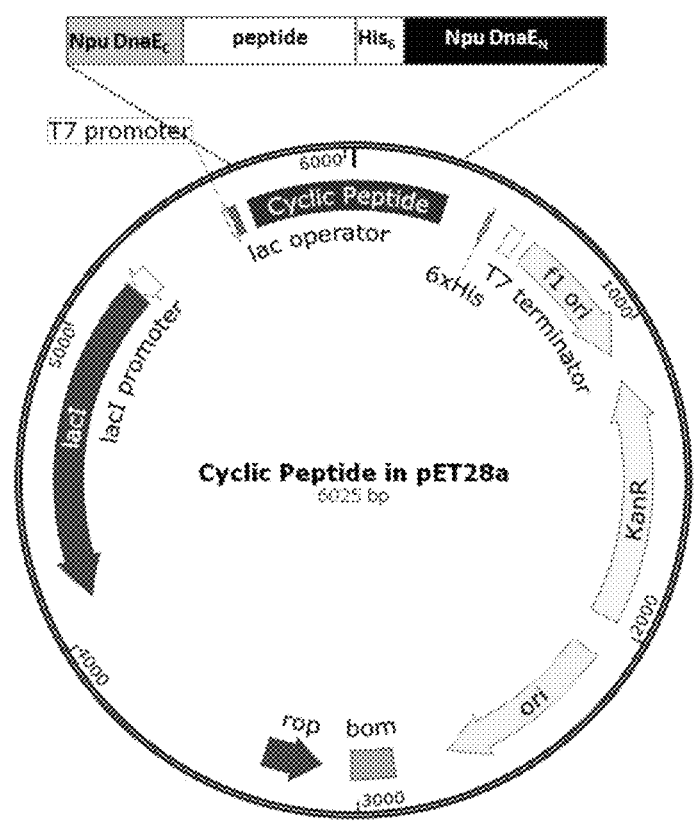
FIG. 4 schematically illustrates the map of a vector for split intein-based cyclic peptide expression.

Unless defined otherwise, all technical and scientific terms used herein have the same meaning as commonly understood by one of ordinary skill in the art to which this invention belongs. All publications and patents referred to herein are incorporated by reference.

Embodiments of the present invention relate to methods useful for constructing a peptide library. In one aspect, the invention relates to a significant improvement of the construction of a peptide library by conventional chemical synthesis. For example, the present invention provides an improved method for the construction of a complete virtual peptide library whereby the cyclic peptides are expressed and purified and the number of cyclic peptides needed to form a complete library is significantly reduced.

According to embodiments of the present invention, the amino acid sequences of the cyclic peptides are rationally designed so that each cyclic peptide can display an array of distinct peptides of different sizes, thus to increase the capacity of the library significantly. Depending on the sizes of the cyclic peptides, each cyclic peptide can display 10 to 100 or even 200 of distinct peptides of a specific size. Therefore, methods according to embodiments of the present invention greatly reduce the peptide number in a peptide library, thus the construction and screening of a peptide library will be performed at significantly reduced costs.

As used herein, the terms a "peptide", a "library", a "tag", a "protein", a "vector", "capacity", "cyclic", "complete" and an "array" are to be taken in their broadest context.

In one general aspect, the present invention relates to an improved method of constructing complete peptide libraries with reduced peptide numbers as compared with the conventional peptide synthesis method. For example, as illustrated in FIGS. 1 and 2, a cyclic peptide can display many shorter peptides. In other words, many short peptides can be displayed by a single cyclic peptide, namely "protein display". Instead of synthesizing 80 different pentapeptides, for example, one cyclic 80-mer peptide can display 80 different pentapeptides, thus to significantly reduce the number of peptides needed to construct a complete pentapeptide library and at the same time increase the screening efficiency. Compared with protein expression, chemical synthesis of relatively long peptides is neither efficient nor cost effective. For example, an 80-mer peptide will take several days for chemical synthesis and head-to-tail peptide cyclization, while the similar cyclic peptide can be readily expressed in a bacteria host overnight. The overall yield of chemically synthesized 80-mer cyclic peptide will be low, while the similar peptide can be readily expressed in an expression host at any scale. In contrast, an embodiment of the present invention provides a method whereby a complete peptide library can be constructed with significantly reduced peptide number, these peptides can be readily expressed and purified, and these peptides can also be readily reproduced at any time using the cloned genes. The method according to the embodiment of the present invention can greatly cut down the time and the cost required for peptide library construction and screening.

Embodiments of the invention relate to protein tags useful in expressing and purifying cyclic peptides. One of the protein tags is GST (glutathione S-transferase), which is commonly used to purify a target protein fused with GST. GST can help the expression of the target protein or peptide. Another common tag is His Tag which contains a string of histidine residues for tagged peptide purification.

In one embodiment of the invention, the protein tag comprises one of the tags selected from, but not limited to, for example, GST, His Tag, Trx, SUMO, CBD, FLAG HA, AviTag, Myc-Tag, SBP, Strep-Tag, Fc-Tag, Halo-Tag, V5, VSV, MBP, etc.

In one embodiment of the invention, the protein tag comprises a combination of the tags selected from, but not limited to, for example, GST, His Tag, Trx, SUMO, CBD, FLAG HA, AviTag, Myc-Tag, SBP, Strep-Tag, Fc-Tag, Halo-Tag, V5, VSV, MBP, etc.

In yet a further embodiment of the invention, tags can be added at any positions of the cyclic peptide to facilitate the expression and purification of the cyclic peptide. The protein tags can be selected from, but not limited to, GST, His Tag, Trx, SUMO, CBD, FLAG HA, AviTag, Myc-Tag, SBP, Strep-Tag, Fc-Tag, Halo-Tag, V5, VSV, MBP, etc.

A protease recognition sequence can also be added between the tag and the peptide so that the peptide can be cleaved from the tag using a protease if necessary.

It is apparent to those skilled in the art that the present invention includes modifications to the above-mentioned embodiments to further improve the library construction. These modifications include, but are not are limited to, adding one or multiple peptide sequences to the above embodiment. For example, one can add some specific amino acids in the peptide sequences to facilitate intein splicing.

A variety of methods can be used to design the peptide sequences to prepare an efficient peptide library in view of the present disclosure. For example, to facilitate the soluble expression of the tagged peptide, peptide sequences containing long stretches of hydrophobic amino acids should be avoided.

It is apparent to those skilled in the art that many different trans-splicing intein systems can be used to produce cyclic peptides. For example, Npu DnaE split intein (Hideo Iwai, Sara Züger, Jennifer Jin, Pui-Hang Tam, Highly efficient protein trans-splicing by a naturally split DnaE intein from *Nostoc punctiforme*. FEBS Letters. 2006, 580:1853-1858), Ssp GyrB split intein, Ssp DnaB split intein, Ssp DnaE split intein, Mxe GyrA split intein, Mtu RecA split intein, and so on, can be used to produce cyclic peptides.

It is also apparent to those skilled in the art that the cyclic peptide can be designed in such a way that the cyclic peptide can display as many as possible distinct short peptides thus to increase the capacity of the peptide library.

According to embodiments illustrated in FIG. 3(A) and FIG. 3(B), an expressed cyclic peptide of 80 amino acids can actually display 80 distinct consecutive tetrapeptide, 80 distinct consecutive pentapeptide, 80 distinct consecutive hexapeptide, 80 distinct consecutive heptapeptide, . . . , 80 distinct consecutive 78-mer peptides, 80 distinct consecutive 79-mer peptides and 80 80-mer peptides, which constitutes 6160 peptides with sizes ranging from 4 to 80 amino acids.

In the above-mentioned embodiments, those skilled in the art will know that the cyclic peptide can even contain up to 200 or more amino acids, although the optimal size will be between 10 to 100. Longer peptides will have higher chances to form tertiary structures in which some peptide sequences will not be exposed for screening.

In the above-mentioned embodiments, those skilled in the art will know that instead of synthesizing 160,000 tetrapeptides chemically, 3,200 or more expressed cyclic 50-mer peptides can constitute or display a complete virtual tetrapeptide library, or 2,000 or more expressed cyclic 80-mer peptides can constitute or display a complete virtual tetrapeptide library.

In the above-mentioned embodiments, those skilled in the art will know that instead of synthesizing 3,200,000 pentapeptides chemically, 64,000 or more expressed cyclic 50-mer peptides can constitute or display a complete virtual pentapeptide library, or 40,000 or more expressed cyclic 80-mer peptides can constitute or display a complete virtual pentapeptide library.

In the above-mentioned embodiments, those skilled in the art will know that some peptides in a peptide library will share high sequence similarity and the number of peptides to construct an efficient peptide library can be greatly reduced by rational designing. Therefore, a smaller number than 3,200 of expressed 50-mer cyclic peptides can constitute an efficient tetrapeptide library. Similarly, a smaller number than 64, 000 of expressed cyclic 50-mer peptides can constitute an efficient pentapeptide library.

In the above-mentioned embodiments, those skilled in the art will know that the cyclic peptide can contain more than 80 amino acids, thus to further reduce the number of the expressed cyclic peptides. Therefore, an even smaller number of expressed peptides can constitute an efficient tetrapeptide, pentapeptide or even hexapeptide library.

In the above-mentioned embodiments, those skilled in the art will know that some peptides in a peptide library will share high sequence similarity and structure similarity, and the number of peptides to construct an efficient peptide library can be further reduced by rational designing. Therefore, a practical number of expressed cyclic peptides can constitute an efficient polypeptide library, such as an octapeptide library, a decapeptide library, or even longer peptide libraries, such as a 15-mer peptide library, a 20-mer peptide library or even a 30-mer peptide library.

In a preferred embodiment, 2, 000 or more expressed His-tagged cyclic 80-mer peptides can be designed, cloned into an expression vector, expressed and purified to constitute a complete virtual tetrapeptide library.

In a further preferred embodiment, 40, 000 or more expressed His-tagged cyclic 80-mer peptides can be designed, cloned into an expression vector, expressed and purified to constitute a complete virtual pentapeptide library, which also constitute a complete virtual tetrapeptide library.

In the above-mentioned embodiments, those skilled in the art will know that other tag or tags can also be used instead of His Tag, the tags can be selected from, but not limited to, GST, Trx, SUMO, CBD, FLAG HA, AviTag, Myc-Tag, SBP, Strep-Tag, Fc-Tag, Halo-Tag, V5, VSV, MBP, etc.

In the above-mentioned embodiments, those skilled in the art will know that the tagged cyclic peptide can contain more than or less than 80 amino acids, thus to further reduce or increase the number of the expressed tagged cyclic peptides to constitute a complete peptide library.

According to embodiments illustrated in FIG. 4, an expression vector of tagged cyclic peptides can be constructed to contain optionally one or more affinity tag DNA sequences, DNA sequences for the two complementary fragments of a split intein (C-terminal intein motif Npu DnaE$_C$ and an N-terminal intein motif Npu DnaE$_N$), a peptide expression DNA sequence, and optionally a protease recognition site which can be used to linearize the cyclic peptide if necessary.

In the above-mentioned embodiments, those skilled in the art will know that the expression vector can be constructed based on, but not limited to, a bacteria expression vector, an yeast expression vector, an insect expression vector, a fungal expression vector, a mammalian expression vector, and a plant expression vector.

In another embodiment of the present invention, the tagged cyclic peptides can be expressed in and purified from an expression host. The expression host is selected from the group consisting of, but not limited to, a bacteria cell, a yeast cell, an insect cell, a fungal cell, a mammalian cell, and a plant cell.

It is readily appreciated by those skilled in the art that, similar methods can also be generally applied for constructing a cyclic peptide library. The designed cyclic peptides are expressed, purified using an affinity tag immobilized on a solid surface, and then used for screening with the peptides still attached to the solid surface. The designed cyclic peptides can also be eluted from the solid surface and then used for screening.

Various embodiments of the invention have now been described. It is to be noted, however, that this description of these specific embodiments is merely illustrative of the principles underlying the inventive concept. It is therefore contemplated that various modifications of the disclosed embodiments will, without departing from the spirit and scope of the invention, be apparent to persons skilled in the art.

The following specific examples are further illustrative of the nature of the invention, it needs to be understood that the invention is not limited thereto.

Protein Display Example

FIG. 3(A) shows the cyclic structure and the amino acid sequence of an 80-mer cyclic peptide, FIG. 3(B) shows that the 80-mer cyclic peptide can display 80 distinct pentapeptides.

The DNA sequence, as shown below, which includes the two Npu DnaE split-intein motifs for the expression of the 80-mer cyclic peptide, was cloned into the pET28a vector as shown in FIG. 4.

(SEQ ID NO: 1)
ATGATCAAGATTGCTACGCGCAAATACTTGGGAAAACAGAACGTTTATG

ATATCGGAGTGGAACGTGACCACAATTTTGCTCTGAAAAACGGATTCAT

CGCAAGTAATTGCTGGGAAAGTGGGAAGATGACCGGTATCGTGAAGTGG

TTTAACGCTGACAAGGGGTTTGGTTTCATTACTCCAGATGACGGTTCTA

AGGATGTTTTCGTTCACTTTTCCGCGATTCAAAACGACGGGTACAAATC

CTTGGATGAGGGCCAAAAAGTCTCATTTACGATTGAATCCGGGGCCAAG

GGTCCCGCAGCAGGAAACGTAACTAGCTTATCCAAAACTCACCACCATC

ATCACTGTTTGTCCTACGAGACCGAGATCCTTACAGTAGAATATGGTTT

GTTACCCATTGGAAAGATCGTGGAGAAGCGTATCGAATGCACAGTGTAC

AGCGTTGATAACAACGGTAACATTTATACCCAACCCGTGGCTCAGTGGC

ATGACCGTGGCGAACAAGAGGTCTTCGAGTATTGCCTTGAGGACGGGTC

TCTGATCCGCGCTACAAAAGATCATAAGTTTATGACCGTTGACGGACAG

ATGCTGCCTATTGACGAAATTTTTGAGCGTGAACTTGACTTAATGCGTG

TCGATAACCTGCCTAATTAA, where the Npu DnaE C-terminal motif (Npu DnaEC) is shown in italic font (SEQ ID NO: 3), the 80-mer cyclic peptide in bold font (SEQ NO: 4), and the Npu DnaE N-terminal motif (Npu DnaEN) in normal font (SEQ ID NO: 5).

The corresponding protein sequence:

(SEQ ID NO: 2)
*MIKIATRKYLGKQNVYDIGVERDHNFALKNGFIASN*CWESGKMTGIVKW

FNADKGFGFITPDDGSKDVFVHFSAIQNDGYKSLDEGQKVSFTIESGAK

GPAAGNVTSLSKTHHHHHCLSYETEILTVEYGLLPIGKIVEKRIECTVY

SVDNNGNIYTQPVAQWHDRGEQEVFEYCLEDGSLIRATKDHKFMTVDGQ

MLPIDEIFERELDLMRVDNLPN, where the Npu DnaE C-terminal motif (Npu DnaE$_C$) is shown in italic font (SEQ ID NO: 88), the 80-mer cyclic peptide in bold font (SEQ ID NO: 89), and the Npu DnaE N-terminal motif (Npu DnaE$_N$) in normal font (SEQ ID NO: 90).

Figure 5:
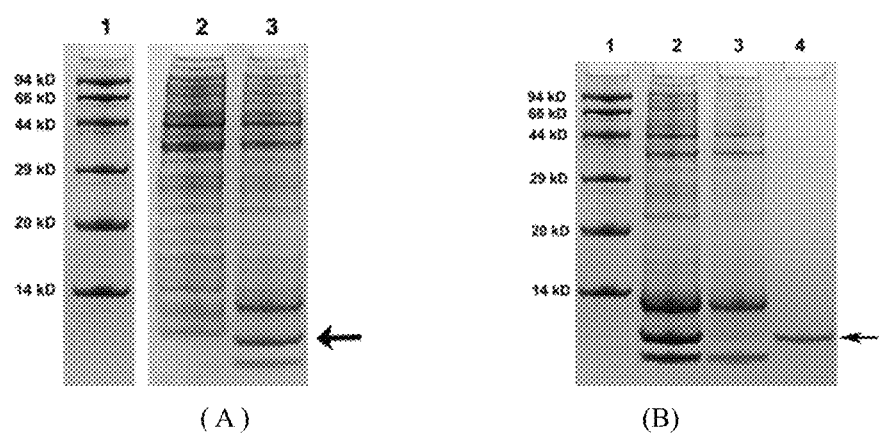
FIG. 5(A) and FIG. 5(B) schematically illustrate the expression and purification of the 80-mer cyclic peptide.

The 80-mer cyclic peptide was expressed in an *E. coli* strain using IPTG as the inducer following standard gene expression method. FIG. 5(A) shows that the 80-mer cyclic peptide was expressed in a soluble form, wherein Lane 1 is a protein marker with the molecular weight listed on the left, Lane 2 is the whole cell lysate without induction, and Lane 3 is the whole cell lysate with 1 mM IPTG induction, the 80-mer cyclic peptide is indicated with an arrow.

The 80-mer cyclic peptide was purified using a Ni-IDA column. The 80-mer cyclic peptide was bound onto the Ni-IDA column and eluted from the column with imidazole. FIG. 5(B) shows that the 80-mer cyclic peptide was purified, wherein Lane 1 is a protein marker with the molecular weight listed on the left, Lane 2 is the whole cell lysate with IPTG induction, Lane 3 is the flow-through of the whole cell lysate sample, and Lane 4 is the purified 80-mer cyclic peptide, which is indicated with an arrow.

All publications and patents referred to herein are incorporated by reference. Various modifications and variations of the described subject matter will be apparent to those skilled in the art without departing from the scope and spirit of the invention. Although the invention has been described in connection with specific embodiments, it should be understood that the invention as claimed should not be unduly limited to these embodiments. Indeed, various modifications for carrying out the invention are obvious to those skilled in the art and are intended to be within the scope of the following claims.

The invention claimed is:

1. A method of constructing a partial or complete peptide library with cyclic peptides including a tetrapeptide library containing some or all of the 160,000 possible tetrapeptide sequences, the method comprising constructing the tetrapeptide library by:
   (i) designing a series of up to 3200 cyclic peptides, each of the cyclic peptides comprising a cyclic peptide of 50 amino acids which displays 50 distinct consecutive and overlapping tetrapeptide sequences, wherein each of the 50 distinct and overlapping consecutive tetrapeptide sequences in each of the cyclic peptides is a distinct tetrapeptide sequence of the 160,000 possible tetrapeptide sequences, and wherein some or all of the 160,000 possible tetrapeptide sequences are contained in the cyclic peptides;
   (ii) constructing a series of expression vectors, each of the expression vectors expressing a single one of the cyclic peptides;
   (iii) expressing and purifying each expressed cyclic peptide; and
   (iv) using each of the expressed and purified cyclic peptides for screening.

2. The method of claim 1, wherein the partial or complete peptide library includes only a partial tetrapeptide library containing some of the 160,000 possible tetrapeptide sequences.

3. The method of claim 1, wherein the cyclic peptides are expressed in and purified from an expression host selected from the group consisting of a bacteria cell, an yeast cell, an insect cell, a fungal cell, a mammalian cell, and a plant cell.

4. The method of claim 1, wherein each of the expression vectors is selected from the group consisting of a bacteria expression vector, an yeast expression vector, an insect expression vector, a fungal expression vector, a mammalian expression vector, and a plant expression vector.

5. The method of claim 1, wherein the cyclic peptides are formed via intein splicing using split inteins, and corresponding linear peptides are fused between a C-terminal intein motif and an N-terminal intein motif.

6. The method of claim 1, wherein the cyclic peptides are expressed in either soluble form or insoluble inclusion bodies, or in both soluble form and insoluble inclusion bodies in a bacteria cell.

7. The method of claim 1, wherein each of the expression vectors comprises:
   a vector backbone;
   a DNA sequence encoding a C-terminal intein motif sequence;
   a DNA sequence encoding one of the cyclic peptides; and
   a DNA sequence encoding an N-terminal intein motif sequence.

* * * * *

SEQUENCE LISTING

<160> NUMBER OF SEQ ID NOS: 90

<210> SEQ ID NO 1
<211> LENGTH: 657
<212> TYPE: DNA
<213> ORGANISM: Artificial Sequence
<220> FEATURE:
<223> OTHER INFORMATION: DNA sequence
<220> FEATURE:
<221> NAME/KEY: CDS
<222> LOCATION: (1)..(657)

<400> SEQUENCE: 1

```
atg atc aag att gct acg cgc aaa tac ttg gga aaa cag aac gtt tat      48
Met Ile Lys Ile Ala Thr Arg Lys Tyr Leu Gly Lys Gln Asn Val Tyr
1               5                   10                  15
```

```
gat atc gga gtg gaa cgt gac cac aat ttt gct ctg aaa aac gga ttc    96
Asp Ile Gly Val Glu Arg Asp His Asn Phe Ala Leu Lys Asn Gly Phe
            20                  25                  30 atc gca agt aat tgc tgg gaa agt ggg aag atg acc ggt atc gtg aag   144
Ile Ala Ser Asn Cys Trp Glu Ser Gly Lys Met Thr Gly Ile Val Lys
        35                  40                  45 tgg ttt aac gct gac aag ggg ttt ggt ttc att act cca gat gac ggt   192
Trp Phe Asn Ala Asp Lys Gly Phe Gly Phe Ile Thr Pro Asp Asp Gly
    50                  55                  60 tct aag gat gtt ttc gtt cac ttt tcc gcg att caa aac gac ggg tac   240
Ser Lys Asp Val Phe Val His Phe Ser Ala Ile Gln Asn Asp Gly Tyr
65                  70                  75                  80 aaa tcc ttg gat gag ggc caa aaa gtc tca ttt acg att gaa tcc ggg   288
Lys Ser Leu Asp Glu Gly Gln Lys Val Ser Phe Thr Ile Glu Ser Gly
                85                  90                  95 gcc aag ggt ccc gca gca gga aac gta act agc tta tcc aaa act cac   336
Ala Lys Gly Pro Ala Ala Gly Asn Val Thr Ser Leu Ser Lys Thr His
            100                 105                 110 cac cat cat cac tgt ttg tcc tac gag acc gag atc ctt aca gta gaa   384
His His His His Cys Leu Ser Tyr Glu Thr Glu Ile Leu Thr Val Glu
        115                 120                 125 tat ggt ttg tta ccc att gga aag atc gtg gag aag cgt atc gaa tgc   432
Tyr Gly Leu Leu Pro Ile Gly Lys Ile Val Glu Lys Arg Ile Glu Cys
    130                 135                 140 aca gtg tac agc gtt gat aac aac ggt aac att tat acc caa ccc gtg   480
Thr Val Tyr Ser Val Asp Asn Asn Gly Asn Ile Tyr Thr Gln Pro Val
145                 150                 155                 160 gct cag tgg cat gac cgt ggc gaa caa gag gtc ttc gag tat tgc ctt   528
Ala Gln Trp His Asp Arg Gly Glu Gln Glu Val Phe Glu Tyr Cys Leu
                165                 170                 175 gag gac ggg tct ctg atc cgc gct aca aaa gat cat aag ttt atg acc   576
Glu Asp Gly Ser Leu Ile Arg Ala Thr Lys Asp His Lys Phe Met Thr
            180                 185                 190 gtt gac gga cag atg ctg cct att gac gaa att ttt gag cgt gaa ctt   624
Val Asp Gly Gln Met Leu Pro Ile Asp Glu Ile Phe Glu Arg Glu Leu
        195                 200                 205 gac tta atg cgt gtc gat aac ctg cct aat taa                       657
Asp Leu Met Arg Val Asp Asn Leu Pro Asn
    210                 215
```

<210> SEQ ID NO 2
<211> LENGTH: 218
<212> TYPE: PRT
<213> ORGANISM: Artificial Sequence
<220> FEATURE:
<223> OTHER INFORMATION: Synthesized

<400> SEQUENCE: 2

```
Met Ile Lys Ile Ala Thr Arg Lys Tyr Leu Gly Lys Gln Asn Val Tyr
1               5                   10                  15

Asp Ile Gly Val Glu Arg Asp His Asn Phe Ala Leu Lys Asn Gly Phe
            20                  25                  30

Ile Ala Ser Asn Cys Trp Glu Ser Gly Lys Met Thr Gly Ile Val Lys
        35                  40                  45

Trp Phe Asn Ala Asp Lys Gly Phe Gly Phe Ile Thr Pro Asp Asp Gly
    50                  55                  60

Ser Lys Asp Val Phe Val His Phe Ser Ala Ile Gln Asn Asp Gly Tyr
65                  70                  75                  80

Lys Ser Leu Asp Glu Gly Gln Lys Val Ser Phe Thr Ile Glu Ser Gly
                85                  90                  95
```

Ala Lys Gly Pro Ala Ala Gly Asn Val Thr Ser Leu Ser Lys Thr His
                100                 105                 110

His His His His Cys Leu Ser Tyr Glu Thr Glu Ile Leu Thr Val Glu
            115                 120                 125

Tyr Gly Leu Leu Pro Ile Gly Lys Ile Val Glu Lys Arg Ile Glu Cys
    130                 135                 140

Thr Val Tyr Ser Val Asp Asn Asn Gly Asn Ile Tyr Thr Gln Pro Val
145                 150                 155                 160

Ala Gln Trp His Asp Arg Gly Glu Gln Glu Val Phe Glu Tyr Cys Leu
                165                 170                 175

Glu Asp Gly Ser Leu Ile Arg Ala Thr Lys Asp His Lys Phe Met Thr
            180                 185                 190

Val Asp Gly Gln Met Leu Pro Ile Asp Glu Ile Phe Glu Arg Glu Leu
    195                 200                 205

Asp Leu Met Arg Val Asp Asn Leu Pro Asn
    210                 215

<210> SEQ ID NO 3
<211> LENGTH: 108
<212> TYPE: DNA
<213> ORGANISM: Artificial Sequence
<220> FEATURE:
<223> OTHER INFORMATION: Npu DnaEC

<400> SEQUENCE: 3
atgatcaaga ttgctacgcg caaatacttg ggaaaacaga acgtttatga tatcggagtg      60
gaacgtgacc acaattttgc tctgaaaaac ggattcatcg caagtaat                  108

<210> SEQ ID NO 4
<211> LENGTH: 240
<212> TYPE: DNA
<213> ORGANISM: Artificial Sequence
<220> FEATURE:
<223> OTHER INFORMATION: 80-mer cyclic peptide

<400> SEQUENCE: 4
tgctgggaaa gtgggaagat gaccggtatc gtgaagtggt ttaacgctga caaggggttt      60
ggtttcatta ctccagatga cggttctaag gatgttttcg ttcactttc cgcgattcaa     120 aacgacgggt acaaatcctt ggatgagggc caaaaagtct catttacgat tgaatccggg    180
gccaagggtc ccgcagcagg aaacgtaact agcttatcca aaactcacca ccatcatcac    240

<210> SEQ ID NO 5
<211> LENGTH: 309
<212> TYPE: DNA
<213> ORGANISM: Artificial Sequence
<220> FEATURE:
<223> OTHER INFORMATION: Npu DnaEN

<400> SEQUENCE: 5
tgtttgtcct acgagaccga gatccttaca gtagaatatg gtttgttacc cattggaaag      60
atcgtggaga gcgtatcga atgcacagtg tacagcgttg ataacaacgg taacattat      120 acccaacccg tggctcagtg gcatgaccgt ggcgaacaag aggtcttcga gtattgcctt    180
gaggacgggt ctctgatccg cgctacaaaa gatcataagt ttatgaccgt tgacggacag    240
atgctgccta ttgacgaaat ttttgagcgt gaacttgact aatgcgtgt cgataacctg    300 cctaattaa                                                            309

```
<210> SEQ ID NO 6
<211> LENGTH: 5
<212> TYPE: PRT
<213> ORGANISM: Artificial Sequence
<220> FEATURE:
<223> OTHER INFORMATION: Sequense DECAF in figure 1 and figure 2

<400> SEQUENCE: 6

Asp Glu Cys Ala Phe
1               5

<210> SEQ ID NO 7
<211> LENGTH: 80
<212> TYPE: PRT
<213> ORGANISM: Artificial Sequence
<220> FEATURE:
<223> OTHER INFORMATION: 80-mer cyclic peptide

<400> SEQUENCE: 7

Cys Trp Glu Ser Gly Lys Met  Thr Gly  Ile Val  Lys Trp Phe Asn Ala
1               5                10                  15

Asp Lys Gly Phe Gly Phe  Ile  Thr Pro Asp Asp Gly Ser  Lys Asp Val
            20                  25                  30

Phe Val His  Phe  Ser Ala Ile  Gln Asn Asp Gly Tyr Lys  Ser Leu Asp
        35                  40                  45

Glu Gly Gln Lys Val  Ser Phe  Thr  Ile Glu  Ser Gly Ala Lys Gly Pro
        50                  55                  60

Ala Ala Gly Asn Val  Thr Ser  Leu Ser Lys  Thr His  His  His  His  His
65                  70                  75                      80

<210> SEQ ID NO 8
<211> LENGTH: 5
<212> TYPE: PRT
<213> ORGANISM: Artificial Sequence
<220> FEATURE:
<223> OTHER INFORMATION: CWESG

<400> SEQUENCE: 8

Cys Trp Glu Ser Gly
1               5

<210> SEQ ID NO 9
<211> LENGTH: 5
<212> TYPE: PRT
<213> ORGANISM: Artificial Sequence
<220> FEATURE:
<223> OTHER INFORMATION: WESGK

<400> SEQUENCE: 9

Trp Glu Ser Gly Lys
1               5

<210> SEQ ID NO 10
<211> LENGTH: 5
<212> TYPE: PRT
<213> ORGANISM: Artificial Sequence
<220> FEATURE:
<223> OTHER INFORMATION: ESGKM

<400> SEQUENCE: 10

Glu Ser Gly Lys Met
1               5

<210> SEQ ID NO 11
```

```
<211> LENGTH: 5
<212> TYPE: PRT
<213> ORGANISM: Artificial Sequence
<220> FEATURE:
<223> OTHER INFORMATION: SGKMT

<400> SEQUENCE: 11

Ser Gly Lys Met Thr
1               5

<210> SEQ ID NO 12
<211> LENGTH: 5
<212> TYPE: PRT
<213> ORGANISM: Artificial Sequence
<220> FEATURE:
<223> OTHER INFORMATION: GKMTG

<400> SEQUENCE: 12

Gly Lys Met Thr Gly
1               5

<210> SEQ ID NO 13
<211> LENGTH: 5
<212> TYPE: PRT
<213> ORGANISM: Artificial Sequence
<220> FEATURE:
<223> OTHER INFORMATION: KMTGI

<400> SEQUENCE: 13

Lys Met Thr Gly Ile
1               5

<210> SEQ ID NO 14
<211> LENGTH: 5
<212> TYPE: PRT
<213> ORGANISM: Artificial Sequence
<220> FEATURE:
<223> OTHER INFORMATION: MTGIV

<400> SEQUENCE: 14

Met Thr Gly Ile Val
1               5

<210> SEQ ID NO 15
<211> LENGTH: 5
<212> TYPE: PRT
<213> ORGANISM: Artificial Sequence
<220> FEATURE:
<223> OTHER INFORMATION: TGIVK

<400> SEQUENCE: 15

Thr Gly Ile Val Lys
1               5

<210> SEQ ID NO 16
<211> LENGTH: 5
<212> TYPE: PRT
<213> ORGANISM: Artificial Sequence
<220> FEATURE:
<223> OTHER INFORMATION: GIVKW

<400> SEQUENCE: 16

Gly Ile Val Lys Trp
1               5

<210> SEQ ID NO 17
<211> LENGTH: 5
```

```
<212> TYPE: PRT
<213> ORGANISM: Artificial Sequence
<220> FEATURE:
<223> OTHER INFORMATION: IVKWF

<400> SEQUENCE: 17

Ile Val Lys Trp Phe
1               5

<210> SEQ ID NO 18
<211> LENGTH: 5
<212> TYPE: PRT
<213> ORGANISM: Artificial Sequence
<220> FEATURE:
<223> OTHER INFORMATION: VKWFN

<400> SEQUENCE: 18

Val Lys Trp Phe Asn
1               5

<210> SEQ ID NO 19
<211> LENGTH: 5
<212> TYPE: PRT
<213> ORGANISM: Artificial Sequence
<220> FEATURE:
<223> OTHER INFORMATION: KWFNA

<400> SEQUENCE: 19

Lys Trp Phe Asn Ala
1               5

<210> SEQ ID NO 20
<211> LENGTH: 5
<212> TYPE: PRT
<213> ORGANISM: Artificial Sequence
<220> FEATURE:
<223> OTHER INFORMATION: WFNAD

<400> SEQUENCE: 20

Trp Phe Asn Ala Asp
1               5

<210> SEQ ID NO 21
<211> LENGTH: 5
<212> TYPE: PRT
<213> ORGANISM: Artificial Sequence
<220> FEATURE:
<223> OTHER INFORMATION: FNADK

<400> SEQUENCE: 21

Phe Asn Ala Asp Lys
1               5

<210> SEQ ID NO 22
<211> LENGTH: 5
<212> TYPE: PRT
<213> ORGANISM: Artificial Sequence
<220> FEATURE:
<223> OTHER INFORMATION: NADKG

<400> SEQUENCE: 22

Asn Ala Asp Lys Gly
1               5

<210> SEQ ID NO 23
<211> LENGTH: 5
<212> TYPE: PRT
```

```
<213> ORGANISM: Artificial Sequence
<220> FEATURE:
<223> OTHER INFORMATION: ADKGF

<400> SEQUENCE: 23

Ala Asp Lys Gly Phe
1               5

<210> SEQ ID NO 24
<211> LENGTH: 5
<212> TYPE: PRT
<213> ORGANISM: Artificial Sequence
<220> FEATURE:
<223> OTHER INFORMATION: DKGFG

<400> SEQUENCE: 24

Asp Lys Gly Phe Gly
1               5

<210> SEQ ID NO 25
<211> LENGTH: 5
<212> TYPE: PRT
<213> ORGANISM: Artificial Sequence
<220> FEATURE:
<223> OTHER INFORMATION: KGFGF

<400> SEQUENCE: 25

Lys Gly Phe Gly Phe
1               5

<210> SEQ ID NO 26
<211> LENGTH: 5
<212> TYPE: PRT
<213> ORGANISM: Artificial Sequence
<220> FEATURE:
<223> OTHER INFORMATION: GFGFI

<400> SEQUENCE: 26

Gly Phe Gly Phe Ile
1               5

<210> SEQ ID NO 27
<211> LENGTH: 5
<212> TYPE: PRT
<213> ORGANISM: Artificial Sequence
<220> FEATURE:
<223> OTHER INFORMATION: FGFIT

<400> SEQUENCE: 27

Phe Gly Phe Ile Thr
1               5

<210> SEQ ID NO 28
<211> LENGTH: 5
<212> TYPE: PRT
<213> ORGANISM: Artificial Sequence
<220> FEATURE:
<223> OTHER INFORMATION: GFITP

<400> SEQUENCE: 28

Gly Phe Ile Thr Pro
1               5

<210> SEQ ID NO 29
<211> LENGTH: 5
<212> TYPE: PRT
<213> ORGANISM: Artificial Sequence
```

```
<220> FEATURE:
<223> OTHER INFORMATION: FITPD

<400> SEQUENCE: 29

Phe Ile Thr Pro Asp
1               5

<210> SEQ ID NO 30
<211> LENGTH: 5
<212> TYPE: PRT
<213> ORGANISM: Artificial Sequence
<220> FEATURE:
<223> OTHER INFORMATION: ITPDD

<400> SEQUENCE: 30

Ile Thr Pro Asp Asp
1               5

<210> SEQ ID NO 31
<211> LENGTH: 5
<212> TYPE: PRT
<213> ORGANISM: Artificial Sequence
<220> FEATURE:
<223> OTHER INFORMATION: TPDDG

<400> SEQUENCE: 31

Thr Pro Asp Asp Gly
1               5

<210> SEQ ID NO 32
<211> LENGTH: 5
<212> TYPE: PRT
<213> ORGANISM: Artificial Sequence
<220> FEATURE:
<223> OTHER INFORMATION: PDDGS

<400> SEQUENCE: 32

Pro Asp Asp Gly Ser
1               5

<210> SEQ ID NO 33
<211> LENGTH: 5
<212> TYPE: PRT
<213> ORGANISM: Artificial Sequence
<220> FEATURE:
<223> OTHER INFORMATION: DDGSK

<400> SEQUENCE: 33

Asp Asp Gly Ser Lys
1               5

<210> SEQ ID NO 34
<211> LENGTH: 5
<212> TYPE: PRT
<213> ORGANISM: Artificial Sequence
<220> FEATURE:
<223> OTHER INFORMATION: DGSKD

<400> SEQUENCE: 34

Asp Gly Ser Lys Asp
1               5

<210> SEQ ID NO 35
<211> LENGTH: 5
<212> TYPE: PRT
<213> ORGANISM: Artificial Sequence
<220> FEATURE:
```

```
<223> OTHER INFORMATION: GSKDV

<400> SEQUENCE: 35

Gly Ser Lys Asp Val
1               5

<210> SEQ ID NO 36
<211> LENGTH: 5
<212> TYPE: PRT
<213> ORGANISM: Artificial Sequence
<220> FEATURE:
<223> OTHER INFORMATION: SKDVF

<400> SEQUENCE: 36

Ser Lys Asp Val Phe
1               5

<210> SEQ ID NO 37
<211> LENGTH: 5
<212> TYPE: PRT
<213> ORGANISM: Artificial Sequence
<220> FEATURE:
<223> OTHER INFORMATION: KDVFV

<400> SEQUENCE: 37

Lys Asp Val Phe Val
1               5

<210> SEQ ID NO 38
<211> LENGTH: 5
<212> TYPE: PRT
<213> ORGANISM: Artificial Sequence
<220> FEATURE:
<223> OTHER INFORMATION: DVFVH

<400> SEQUENCE: 38

Asp Val Phe Val His
1               5

<210> SEQ ID NO 39
<211> LENGTH: 5
<212> TYPE: PRT
<213> ORGANISM: Artificial Sequence
<220> FEATURE:
<223> OTHER INFORMATION: VFVHF

<400> SEQUENCE: 39

Val Phe Val His Phe
1               5

<210> SEQ ID NO 40
<211> LENGTH: 5
<212> TYPE: PRT
<213> ORGANISM: Artificial Sequence
<220> FEATURE:
<223> OTHER INFORMATION: FVHFS

<400> SEQUENCE: 40

Phe Val His Phe Ser
1               5

<210> SEQ ID NO 41
<211> LENGTH: 5
<212> TYPE: PRT
<213> ORGANISM: Artificial Sequence
<220> FEATURE:
<223> OTHER INFORMATION: VHFSA
```

```
<400> SEQUENCE: 41

Val His Phe Ser Ala
1               5

<210> SEQ ID NO 42
<211> LENGTH: 5
<212> TYPE: PRT
<213> ORGANISM: Artificial Sequence
<220> FEATURE:
<223> OTHER INFORMATION: HFSAI

<400> SEQUENCE: 42

His Phe Ser Ala Ile
1               5

<210> SEQ ID NO 43
<211> LENGTH: 5
<212> TYPE: PRT
<213> ORGANISM: Artificial Sequence
<220> FEATURE:
<223> OTHER INFORMATION: FSAIQ

<400> SEQUENCE: 43

Phe Ser Ala Ile Gln
1               5

<210> SEQ ID NO 44
<211> LENGTH: 5
<212> TYPE: PRT
<213> ORGANISM: Artificial Sequence
<220> FEATURE:
<223> OTHER INFORMATION: SAIQN

<400> SEQUENCE: 44

Ser Ala Ile Gln Asn
1               5

<210> SEQ ID NO 45
<211> LENGTH: 5
<212> TYPE: PRT
<213> ORGANISM: Artificial Sequence
<220> FEATURE:
<223> OTHER INFORMATION: AIQND

<400> SEQUENCE: 45

Ala Ile Gln Asn Asp
1               5

<210> SEQ ID NO 46
<211> LENGTH: 5
<212> TYPE: PRT
<213> ORGANISM: Artificial Sequence
<220> FEATURE:
<223> OTHER INFORMATION: IQNDG

<400> SEQUENCE: 46

Ile Gln Asn Asp Gly
1               5

<210> SEQ ID NO 47
<211> LENGTH: 5
<212> TYPE: PRT
<213> ORGANISM: Artificial Sequence
<220> FEATURE:
<223> OTHER INFORMATION: QNDGY
```

```
<400> SEQUENCE: 47

Gln Asn Asp Gly Tyr
1               5

<210> SEQ ID NO 48
<211> LENGTH: 5
<212> TYPE: PRT
<213> ORGANISM: Artificial Sequence
<220> FEATURE:
<223> OTHER INFORMATION: NDGYK

<400> SEQUENCE: 48

Asn Asp Gly Tyr Lys
1               5

<210> SEQ ID NO 49
<211> LENGTH: 5
<212> TYPE: PRT
<213> ORGANISM: Artificial Sequence
<220> FEATURE:
<223> OTHER INFORMATION: DGYKS

<400> SEQUENCE: 49

Asp Gly Tyr Lys Ser
1               5

<210> SEQ ID NO 50
<211> LENGTH: 5
<212> TYPE: PRT
<213> ORGANISM: Artificial Sequence
<220> FEATURE:
<223> OTHER INFORMATION: GYKSL

<400> SEQUENCE: 50

Gly Tyr Lys Ser Leu
1               5

<210> SEQ ID NO 51
<211> LENGTH: 5
<212> TYPE: PRT
<213> ORGANISM: Artificial Sequence
<220> FEATURE:
<223> OTHER INFORMATION: YKSLD

<400> SEQUENCE: 51

Tyr Lys Ser Leu Asp
1               5

<210> SEQ ID NO 52
<211> LENGTH: 5
<212> TYPE: PRT
<213> ORGANISM: Artificial Sequence
<220> FEATURE:
<223> OTHER INFORMATION: KSLDE

<400> SEQUENCE: 52

Lys Ser Leu Asp Glu
1               5

<210> SEQ ID NO 53
<211> LENGTH: 5
<212> TYPE: PRT
<213> ORGANISM: Artificial Sequence
<220> FEATURE:
<223> OTHER INFORMATION: SLDEG

<400> SEQUENCE: 53
```

```
Ser Leu Asp Glu Gly
1               5

<210> SEQ ID NO 54
<211> LENGTH: 5
<212> TYPE: PRT
<213> ORGANISM: Artificial Sequence
<220> FEATURE:
<223> OTHER INFORMATION: LDEGQ

<400> SEQUENCE: 54

Leu Asp Glu Gly Gln
1               5

<210> SEQ ID NO 55
<211> LENGTH: 5
<212> TYPE: PRT
<213> ORGANISM: Artificial Sequence
<220> FEATURE:
<223> OTHER INFORMATION: DEGQK

<400> SEQUENCE: 55

Asp Glu Gly Gln Lys
1               5

<210> SEQ ID NO 56
<211> LENGTH: 5
<212> TYPE: PRT
<213> ORGANISM: Artificial Sequence
<220> FEATURE:
<223> OTHER INFORMATION: EGQKV

<400> SEQUENCE: 56

Glu Gly Gln Lys Val
1               5

<210> SEQ ID NO 57
<211> LENGTH: 5
<212> TYPE: PRT
<213> ORGANISM: Artificial Sequence
<220> FEATURE:
<223> OTHER INFORMATION: GQKVS

<400> SEQUENCE: 57

Gly Gln Lys Val Ser
1               5

<210> SEQ ID NO 58
<211> LENGTH: 5
<212> TYPE: PRT
<213> ORGANISM: Artificial Sequence
<220> FEATURE:
<223> OTHER INFORMATION: QKVSF

<400> SEQUENCE: 58

Gln Lys Val Ser Phe
1               5

<210> SEQ ID NO 59
<211> LENGTH: 5
<212> TYPE: PRT
<213> ORGANISM: Artificial Sequence
<220> FEATURE:
<223> OTHER INFORMATION: KVSFT

<400> SEQUENCE: 59
```

```
Lys Val Ser Phe Thr
1               5

<210> SEQ ID NO 60
<211> LENGTH: 5
<212> TYPE: PRT
<213> ORGANISM: Artificial Sequence
<220> FEATURE:
<223> OTHER INFORMATION: VSFTI

<400> SEQUENCE: 60

Val Ser Phe Thr Ile
1               5

<210> SEQ ID NO 61
<211> LENGTH: 5
<212> TYPE: PRT
<213> ORGANISM: Artificial Sequence
<220> FEATURE:
<223> OTHER INFORMATION: SFTIE

<400> SEQUENCE: 61

Ser Phe Thr Ile Glu
1               5

<210> SEQ ID NO 62
<211> LENGTH: 5
<212> TYPE: PRT
<213> ORGANISM: Artificial Sequence
<220> FEATURE:
<223> OTHER INFORMATION: FTIES

<400> SEQUENCE: 62

Phe Thr Ile Glu Ser
1               5

<210> SEQ ID NO 63
<211> LENGTH: 5
<212> TYPE: PRT
<213> ORGANISM: Artificial Sequence
<220> FEATURE:
<223> OTHER INFORMATION: TIESG

<400> SEQUENCE: 63

Thr Ile Glu Ser Gly
1               5

<210> SEQ ID NO 64
<211> LENGTH: 5
<212> TYPE: PRT
<213> ORGANISM: Artificial Sequence
<220> FEATURE:
<223> OTHER INFORMATION: IESGA

<400> SEQUENCE: 64

Ile Glu Ser Gly Ala
1               5

<210> SEQ ID NO 65
<211> LENGTH: 5
<212> TYPE: PRT
<213> ORGANISM: Artificial Sequence
<220> FEATURE:
<223> OTHER INFORMATION: ESGAK

<400> SEQUENCE: 65

Glu Ser Gly Ala Lys
```

```
<210> SEQ ID NO 66
<211> LENGTH: 5
<212> TYPE: PRT
<213> ORGANISM: Artificial Sequence
<220> FEATURE:
<223> OTHER INFORMATION: SGAKG

<400> SEQUENCE: 66

Ser Gly Ala Lys Gly
1               5

<210> SEQ ID NO 67
<211> LENGTH: 5
<212> TYPE: PRT
<213> ORGANISM: Artificial Sequence
<220> FEATURE:
<223> OTHER INFORMATION: GAKGP

<400> SEQUENCE: 67

Gly Ala Lys Gly Pro
1               5

<210> SEQ ID NO 68
<211> LENGTH: 5
<212> TYPE: PRT
<213> ORGANISM: Artificial Sequence
<220> FEATURE:
<223> OTHER INFORMATION: AKGPA

<400> SEQUENCE: 68

Ala Lys Gly Pro Ala
1               5

<210> SEQ ID NO 69
<211> LENGTH: 5
<212> TYPE: PRT
<213> ORGANISM: Artificial Sequence
<220> FEATURE:
<223> OTHER INFORMATION: KGPAA

<400> SEQUENCE: 69

Lys Gly Pro Ala Ala
1               5

<210> SEQ ID NO 70
<211> LENGTH: 5
<212> TYPE: PRT
<213> ORGANISM: Artificial Sequence
<220> FEATURE:
<223> OTHER INFORMATION: GPAAG

<400> SEQUENCE: 70

Gly Pro Ala Ala Gly
1               5

<210> SEQ ID NO 71
<211> LENGTH: 5
<212> TYPE: PRT
<213> ORGANISM: Artificial Sequence
<220> FEATURE:
<223> OTHER INFORMATION: PAAGN

<400> SEQUENCE: 71

Pro Ala Ala Gly Asn
1               5
```

```
<210> SEQ ID NO 72
<211> LENGTH: 5
<212> TYPE: PRT
<213> ORGANISM: Artificial Sequence
<220> FEATURE:
<223> OTHER INFORMATION: AAGNV

<400> SEQUENCE: 72

Ala Ala Gly Asn Val
1               5

<210> SEQ ID NO 73
<211> LENGTH: 5
<212> TYPE: PRT
<213> ORGANISM: Artificial Sequence
<220> FEATURE:
<223> OTHER INFORMATION: AGNVT

<400> SEQUENCE: 73

Ala Gly Asn Val Thr
1               5

<210> SEQ ID NO 74
<211> LENGTH: 5
<212> TYPE: PRT
<213> ORGANISM: Artificial Sequence
<220> FEATURE:
<223> OTHER INFORMATION: GNVTS

<400> SEQUENCE: 74

Gly Asn Val Thr Ser
1               5

<210> SEQ ID NO 75
<211> LENGTH: 5
<212> TYPE: PRT
<213> ORGANISM: Artificial Sequence
<220> FEATURE:
<223> OTHER INFORMATION: NVTSL

<400> SEQUENCE: 75

Asn Val Thr Ser Leu
1               5

<210> SEQ ID NO 76
<211> LENGTH: 5
<212> TYPE: PRT
<213> ORGANISM: Artificial Sequence
<220> FEATURE:
<223> OTHER INFORMATION: VTSLS

<400> SEQUENCE: 76

Val Thr Ser Leu Ser
1               5

<210> SEQ ID NO 77
<211> LENGTH: 5
<212> TYPE: PRT
<213> ORGANISM: Artificial Sequence
<220> FEATURE:
<223> OTHER INFORMATION: TSLSK

<400> SEQUENCE: 77

Thr Ser Leu Ser Lys
1               5
```

<210> SEQ ID NO 78
<211> LENGTH: 5
<212> TYPE: PRT
<213> ORGANISM: Artificial Sequence
<220> FEATURE:
<223> OTHER INFORMATION: SLSKT

<400> SEQUENCE: 78

Ser Leu Ser Lys Thr
1               5

<210> SEQ ID NO 79
<211> LENGTH: 5
<212> TYPE: PRT
<213> ORGANISM: Artificial Sequence
<220> FEATURE:
<223> OTHER INFORMATION: LSKTH

<400> SEQUENCE: 79

Leu Ser Lys Thr His
1               5

<210> SEQ ID NO 80
<211> LENGTH: 5
<212> TYPE: PRT
<213> ORGANISM: Artificial Sequence
<220> FEATURE:
<223> OTHER INFORMATION: SKTHH

<400> SEQUENCE: 80

Ser Lys Thr His His
1               5

<210> SEQ ID NO 81
<211> LENGTH: 5
<212> TYPE: PRT
<213> ORGANISM: Artificial Sequence
<220> FEATURE:
<223> OTHER INFORMATION: KTHHH

<400> SEQUENCE: 81

Lys Thr His His His
1               5

<210> SEQ ID NO 82
<211> LENGTH: 5
<212> TYPE: PRT
<213> ORGANISM: Artificial Sequence
<220> FEATURE:
<223> OTHER INFORMATION: THHHH

<400> SEQUENCE: 82

Thr His His His His
1               5

<210> SEQ ID NO 83
<211> LENGTH: 5
<212> TYPE: PRT
<213> ORGANISM: Artificial Sequence
<220> FEATURE:
<223> OTHER INFORMATION: HHHHH

<400> SEQUENCE: 83

His His His His His
1               5

```
<210> SEQ ID NO 84
<211> LENGTH: 5
<212> TYPE: PRT
<213> ORGANISM: Artificial Sequence
<220> FEATURE:
<223> OTHER INFORMATION: HHHHC

<400> SEQUENCE: 84

His His His His Cys
1               5

<210> SEQ ID NO 85
<211> LENGTH: 5
<212> TYPE: PRT
<213> ORGANISM: Artificial Sequence
<220> FEATURE:
<223> OTHER INFORMATION: HHHCW

<400> SEQUENCE: 85

His His His Cys Trp
1               5

<210> SEQ ID NO 86
<211> LENGTH: 5
<212> TYPE: PRT
<213> ORGANISM: Artificial Sequence
<220> FEATURE:
<223> OTHER INFORMATION: HHCWE

<400> SEQUENCE: 86

His His Cys Trp Glu
1               5

<210> SEQ ID NO 87
<211> LENGTH: 5
<212> TYPE: PRT
<213> ORGANISM: Artificial Sequence
<220> FEATURE:
<223> OTHER INFORMATION: HCWES

<400> SEQUENCE: 87

His Cys Trp Glu Ser
1               5

<210> SEQ ID NO 88
<211> LENGTH: 36
<212> TYPE: PRT
<213> ORGANISM: Artificial Sequence
<220> FEATURE:
<223> OTHER INFORMATION: Npu DnaEc

<400> SEQUENCE: 88

Met Ile Lys Ile Ala Thr Arg Lys Tyr Leu Gly Lys Gln Asn Val Tyr
1               5                   10                  15

Asp Ile Gly Val Glu Arg Asp His Asn Phe Ala Leu Lys Asn Gly Phe
            20                  25                  30

Ile Ala Ser Asn
        35

<210> SEQ ID NO 89
<211> LENGTH: 80
<212> TYPE: PRT
<213> ORGANISM: Artificial Sequence
<220> FEATURE:
<223> OTHER INFORMATION: 80-mer cyclic peptide

<400> SEQUENCE: 89
```

-continued

```
Cys Trp Glu Ser Gly Lys Met Thr Gly Ile Val Lys Trp Phe Asn Ala
1               5                   10                  15

Asp Lys Gly Phe Gly Phe Ile Thr Pro Asp Asp Gly Ser Lys Asp Val
                20                  25                  30

Phe Val His Phe Ser Ala Ile Gln Asn Asp Gly Tyr Lys Ser Leu Asp
            35                  40                  45

Glu Gly Gln Lys Val Ser Phe Thr Ile Glu Ser Gly Ala Lys Gly Pro
            50                  55                  60

Ala Ala Gly Asn Val Thr Ser Leu Ser Lys Thr His His His His His
65                  70                  75                  80
```

<210> SEQ ID NO 90
<211> LENGTH: 102
<212> TYPE: PRT
<213> ORGANISM: Artificial Sequence
<220> FEATURE:
<223> OTHER INFORMATION: Npu DnaEN

<400> SEQUENCE: 90

```
Cys Leu Ser Tyr Glu Thr Glu Ile Leu Thr Val Glu Tyr Gly Leu Leu
1               5                   10                  15

Pro Ile Gly Lys Ile Val Glu Lys Arg Ile Glu Cys Thr Val Tyr Ser
                20                  25                  30

Val Asp Asn Asn Gly Asn Ile Tyr Thr Gln Pro Val Ala Gln Trp His
            35                  40                  45

Asp Arg Gly Glu Gln Glu Val Phe Glu Tyr Cys Leu Glu Asp Gly Ser
            50                  55                  60

Leu Ile Arg Ala Thr Lys Asp His Lys Phe Met Thr Val Asp Gly Gln
65                  70                  75                  80

Met Leu Pro Ile Asp Glu Ile Phe Glu Arg Glu Leu Asp Leu Met Arg
                85                  90                  95

Val Asp Asn Leu Pro Asn
                100
```